United States Patent [19]
Kameswaran

[11] Patent Number: 6,133,455
[45] Date of Patent: Oct. 17, 2000

[54] PROCESS FOR THE PREPARATION OF 2-ARYL-5(PERFLUORO-ALKYL) PYRROLE COMPOUNDS FROM N-(ARYLMETHYLENE)-1-CHLORO-1-(PERFLUOROALKYL) METHYLAMINE COMPOUNDS

[75] Inventor: Venkataraman Kameswaran, Trenton, N.J.

[73] Assignee: American Cyanamid Company, Madison, N.J.

[21] Appl. No.: 09/246,326

[22] Filed: Feb. 9, 1999

Related U.S. Application Data

[60] Provisional application No. 60/074,097, Feb. 9, 1998.

[51] Int. Cl.[7] .................. C07D 207/30; C07D 207/34; C07D 207/42; C07D 405/04; C07D 409/04

[52] U.S. Cl. .................. 548/517; 548/525; 548/526; 548/527; 548/536; 548/557; 548/560; 548/562; 548/570; 548/574

[58] Field of Search ..................... 548/517, 536, 548/557, 560, 562, 525, 526, 527, 570, 574

[56] References Cited

U.S. PATENT DOCUMENTS

| | | | |
|---|---|---|---|
| 5,010,098 | 4/1991 | Brown et al. | 514/426 |
| 5,068,390 | 11/1991 | Kuhn et al. | 558/561 |
| 5,145,986 | 9/1992 | Kameswaran | 548/531 |
| 5,359,090 | 10/1994 | Doehner et al. | 548/561 |
| 5,426,225 | 6/1995 | Kameswaran | 564/212 |
| 5,446,170 | 8/1995 | Kameswaran | 548/517 |
| 5,449,789 | 9/1995 | Kameswaran | 548/561 |

OTHER PUBLICATIONS

K. Tanaka et al, Chemistry Letters, pp. 1463–1464 (1983).

*Primary Examiner*—Joseph McKane
*Assistant Examiner*—Jane C. Oswecki
*Attorney, Agent, or Firm*—John W. Hogan

[57] ABSTRACT

There is provided a process for the preparation of 2-aryl-5-(perfluoroalkyl)pyrrole compounds from N-(arylmethylene)-1-chloro-1-(perfluoroalkyl)methylamine compounds. The 2-aryl-5-(perfluoroalkyl)pyrrole compounds are useful for the control of insect and acarid pests, and may also be used to prepare other pesticidal arylpyrrole compounds.

In addition, the present invention provides N-(arylmethylene)-1-chloro-1-(perfluoroalkyl)methylamine compounds which are useful as intermediates in the preparation of arylpyrrole compounds.

11 Claims, No Drawings

PROCESS FOR THE PREPARATION OF 2-ARYL-5(PERFLUORO-ALKYL) PYRROLE COMPOUNDS FROM N-(ARYLMETHYLENE)-1-CHLORO-1-(PERFLUOROALKYL) METHYLAMINE COMPOUNDS

This application claims the benefit of Provisional Application No. 60/074,097 filed Feb. 9, 1998.

BACKGROUND OF THE INVENTION

2-Aryl-5-(perfluoroalkyl)pyrrole compounds are useful as insecticidal and acaricidal agents. In addition, those compounds are also useful for the preparation of other insecticidal and acaricidal agents. In particular, 2-aryl-5-(perfluoroalkyl)pyrrole compounds are key intermediates in the preparation of arylpyrrole compounds such as chlorfenapyr. Accordingly, there is an ongoing search to discover new methods for the preparation of 2-aryl-5-(perfluoralkyl) pyrrole compounds.

U.S. Pat. No. 5,145,986 discloses that 2-aryl-5-(trifluoromethyl)pyrrole compounds may be prepared from N-(substituted benzyl)-2,2,2-trifluoroacetimidoyl chloride compounds. U.S. Pat. Nos. 5,446,170 and 5,426,225 disclose that 2-aryl-5-(trifluoromethyl)pyrrole compounds may be obtained in several steps from the appropriate aldehyde. The processes described in U.S. Pat. Nos. 5,446,170 and 5,426,225 require the use of an aminonitrile intermediate which is obtained via the Strecker synthesis from the appropriate aldehyde. However, the use of the Strecker synthesis is not entirely satisfactory because of cyanide containing waste streams.

It is, therefore, an object of the present invention to provide a new process for the preparation of 2-aryl-5-(perfluoroalkyl)pyrrole compounds which avoids the use of the Strecker synthesis.

It is also an object of this invention to provide a new process for the preparation of arylpyrrole compounds such as chlorfenapyr.

A further object of the present invention is to provide new intermediate compounds which are useful in the processes described hereinbelow.

Those and other objects of the present invention will become more apparent from the detailed description thereof set forth below.

SUMMARY OF THE INVENTION

The present invention provides a new process for the preparation of 2-aryl-5-(perfluoroalkyl)pyrrole compounds having the structural formula I

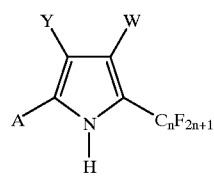

(I)

wherein
W is hydrogen or $C_mF_{2m+1}$;
Y is CN, $NO_2$ or $CO_2R$;
R is $C_1-C_4$alkyl;
m and n are each independently an integer of 1, 2, 3, 4, 5, 6, 7 or 8;

A is

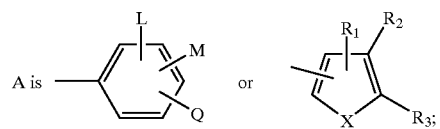

L is hydrogen or halogen;
M and Q are each independently hydrogen, halogen, CN, $NO_2$, $C_1-C_4$alkyl, $C_1-C_4$haloalkyl, $C_1-C_4$alkoxy, $C_1-C_4$haloalkoxy, $C_1-C_4$alkylthio, $C_1-C_4$haloalkylthio, $C_1-C_4$alkylsulfinyl, $C_1-C_4$haloalkylsulfinyl, $C_1-C_4$alkylsulfonyl, $C_1-C_4$haloalkylsulfonyl or when M and Q are on adjacent positions they may be taken together with the carbon atoms to which they are attached to form a ring in which MQ represents the structure —$OCH_2O$—, —$OCF_2O$— or —CH=CH—CH=CH—;
$R_1$, $R_2$ and $R_3$ are each independently hydrogen, halogen, $NO_2$, CHO or $R_2$ and $R_3$ may be taken together with the atoms to which they are attached to form a ring in which $R_2R_3$ is represented by the structure

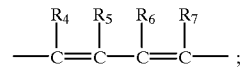

$R_4$, $R_5$, $R_6$ and $R_7$ are each independently hydrogen, halogen, CN or $NO_2$; and
X is O or S which process comprises reacting an N-(arylmethylene)-1-chloro-1-(perfluoroalkyl)methylamine compound having the structural formula II

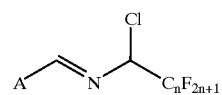

(II)

wherein A and n are as described above with a dieneophile compound having the structural formula III

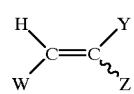

(III)

wherein W and Y are as described above and Z is Cl, Br or I, and a base in the presence of a solvent.

The present invention further provides novel N-(arylmethylene)-1-chloro-1-(perfluoroalkyl)methylamine compounds having the structural formula II

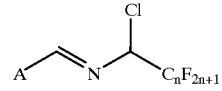

(II)

wherein n and A are as described hereinabove, provided that when A is unsubstituted phenyl, p-chlorophenyl or p-methylphenyl, n is an integer other than 1.

DETAILED DESCRIPTION OF THE INVENTION

The process of the present invention preferably comprises reacting an N-(arylmethylene)-1-chloro-1-(perfluoroalkyl)

methylamine compound of formula II with at least about one molar equivalent, preferably about one to four molar equivalents, of a dienophile compound of formula III and at least about one molar equivalent, preferably about one to four molar equivalents, of a base in the presence of a solvent preferably at a temperature range of about 5° C. to 100° C. to form 2-aryl-5-(perfluoroalkyl)pyrrole compounds of formula I.

Alternatively, the formula I compounds may be prepared by forming the formula III dienophile compounds in situ. This process comprises reacting an N-(arylmethylene)-1-chloro-1-(perfluoroalkyl)methylamine compound of formula II with preferably about one to four molar equivalents of an α,β-dihalo compound having the structural formula IV

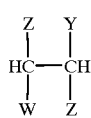

(IV)

wherein W and Y are as described hereinabove and Z is Cl, Br or I, and at least about two molar equivalents, preferably about two to five molar equivalents, of a base in the presence of a solvent preferably at a temperature range of about 5° C. to 100° C. to form 2-aryl-5-(perfluoroalkyl)pyrrole compounds of formula I.

Advantageously, the present invention provides new processes for the preparation of 2-aryl-5-(perfluoroalkyl)pyrrole compounds which avoid the use of the Strecker synthesis.

The formula I compounds of this invention may be isolated by conventional procedures such as dilution of the reaction mixture with water and filtration or, alternatively, extraction with a suitable solvent. Suitable extraction solvents include water-immiscible solvents such as ether, ethyl acetate, toluene, methylene chloride and the like.

Bases suitable for use in this invention include tri-($C_1$–$C_6$alkyl)amines such as trimethylamine, triethylamine, tripropylamine, tributylamine, diisopropylethylamine and the like; alkali metal carbonates such as potassium carbonate and sodium carbonate; alkali metal hydroxides such as potassium hydroxide and sodium hydroxide; alkali metal acetates such as potassium acetate and sodium acetate; and heterocyclic tertiary amines including, but not limited to, 1,8-diazabicyclo[5.4.0]undec-7-ene (DBU); 1,5-diazabicyclo[4.3.0]non-5-ene (DBN); 1,4-diazabicyclo[2.2.2]-octane; pyridine; substituted pyridines such as 2,6-dimethylpyridine, 2-methylpyridine, 3-methylpyridine, 4-methylpyridine and the like; quinoline; and substituted quinolines. Preferred bases include tri-($C_1$–$C_6$alkyl)-amines, 1,8-diazabicyclo[5.4.0]undec-7-ene, 1,5-diazabicyclo[4.3.0]non-5-ene, 1,4-diazabicyclo[2.2.2]-octane, potassium carbonate and sodium carbonate.

Solvents suitable for use in the present invention include, but are not limited to, carboxylic acid amides such as N,N-dimethylformamide, N,N-dimethylacetamide and the like; N-substituted pyrrolidinones such as N-methylpyrrolidinone and the like; nitriles such as acetonitrile, propionitrile and the like; halogenated hydrocarbons such as methylene chloride, chloroform, carbon tetrachloride and the like; ethers such as tetrahydrofuran, dioxane and the like; sulfoxides such as dimethyl sulfoxide and the like; and mixtures thereof. Preferred solvents include carboxylic acid amides and nitriles and mixtures thereof. N,N-dimethylformamide and acetonitrile and mixtures thereof are especially preferred for use in the present invention.

Exemplary of halogen hereinabove are fluorine, chlorine, bromine and iodine. The terms "$C_1$–$C_4$haloalkyl", "$C_1$–$C_4$haloalkoxy", "$C_1$–$C_4$haloalkylthio", "$C_1$–$C_4$haloalkylsulfinyl" and "$C_1$–$C_4$haloalkylsulfonyl" are defined as a $C_1$–$C_4$alkyl, $C_1$–$C_4$alkoxy, $C_1$–$C_4$alkylthio, $C_1$–$C_4$alkylsulfinyl or $C_1$–$C_4$alkylsulfonyl group substituted with one or more halogen atoms, respectively.

The present invention is especially useful for the preparation of formula I compounds wherein W is hydrogen;

Y is CN;

n is 1 or 2;

A is 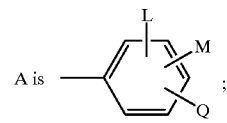;

L is hydrogen or halogen; and

M and Q are each independently hydrogen, halogen, $C_1$–$C_4$haloalkyl or $C_1$–$C_4$haloalkoxy.

In particular, the present invention is useful for the preparation of 2-(p-chlorophenyl)-5-(trifluoromethyl)pyrrole-3-carbonitrile;

2-(3,5-dichlorophenyl)-5-(trifluoromethyl)pyrrole-3-carbonitrile;

2-(3,4-dichlorophenyl)-5-(trifluoromethyl)pyrrole-3-carbonitrile; and

2-[4-(trifluoromethyl)phenyl]-5-(trifluoromethyl)pyrrole-3-carbonitrile, among others.

The present invention also relates to novel N-(arylmethylene)-1-chloro-1-(perfluoroalkyl)methylamine compounds having the structural formula II

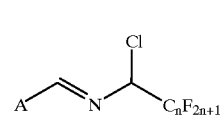

(II)

wherein n is an integer of 1, 2, 3, 4, 5, 6, 7 or 8;

A is 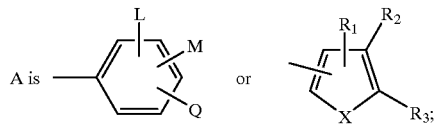;

L is hydrogen or halogen;

M and Q are each independently hydrogen, halogen, CN, $NO_2$, $C_1$–$C_4$alkyl, $C_1$–$C_4$haloalkyl, $C_1$–$C_4$alkoxy, $C_1$–$C_4$haloalkoxy, $C_1$–$C_4$alkylthio, $C_1$–$C_4$haloalkylthio, $C_1$–$C_4$alkylsulfinyl, $C_1$–$C_4$haloalkylsulfinyl, $C_1$–$C_4$alkylsulfonyl, $C_1$–$C_4$haloalkylsulfonyl or when M and Q are on adjacent positions they may be taken together with the carbon atoms to which they are attached to form a ring in which MQ represents the structure —$OCH_2O$—, —$OCF_2O$— or —CH=CH—CH=CH—;

$R_1$, $R_2$ and $R_3$ are each independently hydrogen, halogen, $NO_2$, CHO or $R_2$ and $R_3$ may be taken together with the atoms to which they are attached to form a ring in which $R_2R_3$ is represented by the structure

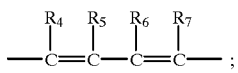

$R_4$, $R_5$, $R_6$ and $R_7$ are each independently hydrogen, halogen, CN or $NO_2$; and X is 0 or S, provided that when A is unsubstituted phenyl, p-chlorophenyl or p-methylphenyl, n is an integer other than 1.

Preferred novel formula II compounds of this invention are those wherein n is 1 or 2;

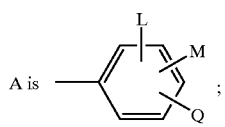

L is hydrogen or halogen; and

M and Q are each independently halogen, $C_1$–$C_4$haloalkyl or $C_1$–$C_4$haloalkoxy.

Novel formula II compounds which are particularly useful in the processes of this invention include 1-chloro-N-(3,5-dichlorobenzylidine)-2,2,2-trifluoroethylamine;

1-chloro-N-(3,4-dichlorobenzylidine)-2,2,2-trifluoroethylamine; and 1-chloro-2,2,2-trifluoro-N-[4-(trifluoromethyl)-benzylidine]ethylamine, among others.

Starting N-(arylmethylene)-1-chloro-1-(perfluoroalkyl) methylamine compounds of formula II may be prepared, as shown in Flow Diagram I, by isomerizing an N-(arylmethyl) perfluoroalkylformimidoyl chloride compound having the structural formula V with a tertiary amine optionally at an elevated temperature according to the procedures described in Chemistry Letters, pp. 1463–1464 (1983).

FLOW DIAGRAM I

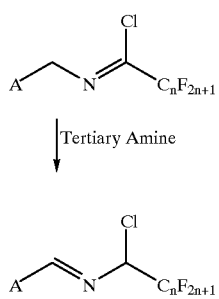

Tertiary amines suitable for use to isomerize the formula V compounds include tri-($C_1$–$C_6$alkyl)amines such as triethylamine, tripropylamine, diisopropylethylamine and the like; and heterocyclic tertiary amines including, but not limited to, 1,8-diazabicyclo[5.4.0]undec-7-ene; 1,5-diazabicyclo[4.3.0]non-5-ene; pyridine; substituted pyridines such as 2,6-dimethylpyridine, 2-methylpyridine, 3-methylpyridine, 4-methylpyridine and the like; quinoline; and substituted quinolines. Preferred tertiary amines include tri-($C_1$–$C_6$alkyl) amines, 1,8-diazabicyclo[5.4.0]undec-7-ene and 1,5-diazabicyclo-[4.3.0]non-5-ene.

In a preferred embodiment of the present invention, the formula V compound is isomerized with a tertiary amine in the presence of a solvent at a temperature range of about 15° C. to 60° C. Solvents suitable for use in the preparation of the formula II compounds include aromatic hydrocarbons such as toluene, benzene, xylenes and the like and mixtures thereof.

The N-(arylmethyl)perfluroalkylformimidoyl chloride compounds of formula V may be prepared according to the procedures described in U.S. Pat. No. 5,145,986 and Chemistry Letters, pp. 1463–1464 (1983).

Starting formula III dienophile compounds are known in the art and may be prepared using conventional procedures. Compounds of formulas III and IV wherein W is $C_mF_{2m+1}$ may be prepared according to the procedures described in U.S. Pat. No. 5,068,390.

The formula I compounds are useful for the control of insect and acarid pests. In addition, the formula I compounds may be used to prepare other arylpyrrole insecticidal and acaricidal agents having the structural formula VI

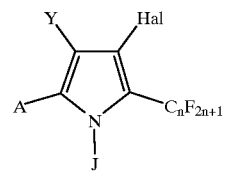

(VI)

wherein

Y is CN, $NO_2$ or $CO_2R$;

R is $C_1$–$C_4$alkyl;

n is an integer of 1, 2, 3, 4, 5, 6, 7 or 8;

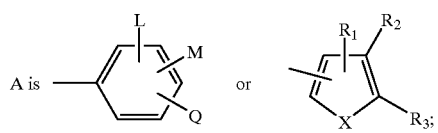

L is hydrogen or halogen;

M and Q are each independently hydrogen, halogen, CN, $NO_2$, $C_1$–$C_4$alkyl, $C_1$–$C_4$haloalkyl, $C_1$–$C_4$alkoxy, $C_1$–$C_4$haloalkoxy, $C_1$–$C_4$alkylthio, $C_1$–$C_4$haloalkylthio, $C_1$–$C_4$alkylsulfinyl, $C_1$–$C_4$haloalkylsulfinyl, $C_1$–$C_4$alkylsulfonyl, $C_1$–$C_4$haloalkylsulfonyl or when M and Q are on adjacent positions they may be taken together with the carbon atoms to which they are attached to form a ring in which MQ represents the structure —$OCH_2O$—, —$OCF_2O$— or —CH=CH—CH=CH—;

$R_1$, $R_2$ and $R_3$ are each independently hydrogen, halogen, $NO_2$, CHO or $R_2$ and $R_3$ may be taken together with the atoms to which they are attached to form a ring in which $R_2R_3$ is represented by the structure

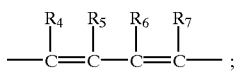

$R_4$, $R_5$, $R_6$ and $R_7$ are each independently hydrogen, halogen, CN or $NO_2$;

X is O or S;

Hal is a halogen atom; and

J is hydrogen or $C_1$–$C_6$alkoxymethyl.

The present invention is especially useful for the preparation of arylpyrrole compounds of formula VI wherein Y is CN;

n is 1 or 2;

A is 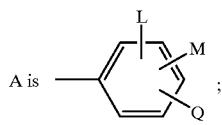 ;

L is hydrogen or halogen;

M and Q are each independently hydrogen, halogen, $C_1$–$C_4$haloalkyl or $C_1$–$C_4$haloalkoxy;

Hal is Br or Cl; and

J is hydrogen or ethoxymethyl.

In particular, the present invention is useful for the preparation of formula VI arylpyrrole compounds such as 4-bromo-2-(p-chlorophenyl)-1-(ethoxymethyl)-5-(trifluoromethyl)pyrrole-3-carbonitrile (chlorfenapyr);

4-bromo-2-(3,4-dichlorophenyl)-1-(ethoxymethyl)-5-(trifluoromethyl)pyrrole-3-carbonitrile; and 4-bromo-2-(p-chlorophenyl)-5-(trifluoromethyl)pyrrole-3-carbonitrile, among others.

Advantageously, formula VI arylpyrrole compounds may be prepared by a process which comprises:

(a) reacting an N-(arylmethylene)-1-chloro-1-(perfluoroalkyl)methylamine compound of formula II with a dienophile compound having the structural formula VII

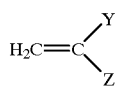
(VII)

wherein Y is as described above and Z is Cl, Br or I, and a base in the presence of a solvent to form a 2-aryl-5-(perfluoroalkyl)pyrrole compound having the structural formula VIII

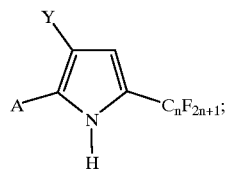
(VIII)

(b) halogenating the formula VIII compound to form the arylpyrrole compound of formula VI wherein J is hydrogen; and (c) optionally alkoxymethylating the formula VI compound wherein J is hydrogen to form the formula VI arylpyrrole compound wherein J is $C_1$–$C_6$alkoxymethyl.

Alternatively, arylpyrrole compounds of formula VI may be prepared by a process which comprises:

(a) reacting an N-(arylmethylene)-1-chloro-1-(perfluoroalkyl)methylamine compound of formula II with an α,β-dihalo compound having the structural formula IX

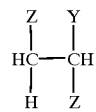
(IX)

wherein Y is as described above and Z is Cl, Br or I, and at least about two molar equivalents of a base in the presence of a solvent to form a 2-aryl-5-(perfluoroalkyl)pyrrole compound having the structural formula VIII

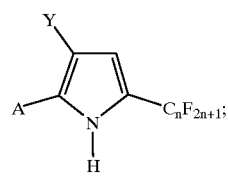
(VIII)

(b) halogenating the formula VIII compound to form the arylpyrrole compound of formula VI wherein J is hydrogen; and (c) optionally alkoxymethylating the formula VI compound wherein J is hydrogen to form the formula VI arylpyrrole compound wherein J is $C_1$–$C_6$alkoxymethyl.

Halogenation methods may be any known methods such as those described in U.S. Pat. Nos. 5,010,098 and 5,449,789.

Alkoxymethylation procedures suitable for use in this invention include conventional procedures known in the art (see, e.g., U.S. Pat. Nos. 5,010,098 and 5,359,090). In a preferred embodiment of this invention, the alkoxymethylation procedure comprises reacting a formula VI compound wherein J is hydrogen with a di-($C_1$–$C_6$alkoxy)methane compound, N,N-dimethylformamide and phosphorous oxychloride in the presence of an aprotic solvent to form a reaction mixture and treating the reaction mixture with a tertiary amine.

In order to facilitate a further understanding of this invention, the following examples are presented primarily for the purpose of illustrating more specific details thereof. The scope of the invention should not be deemed limited by the examples, but encompasses the entire subject matter defined in the claims.

EXAMPLE 1

Preparation of 1-Chloro-N-(P-chlorobenzylidine)-2,2,2-trifluoroethylamine

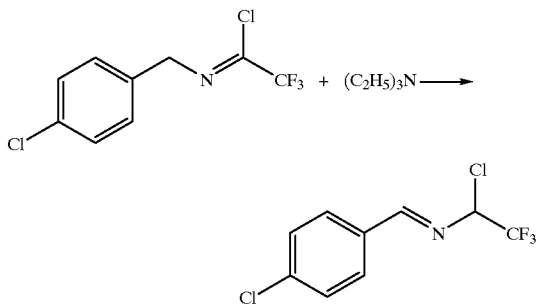

A solution of N-(p-chlorobenzyl)-2,2,2-trifluoroacetimidoyl chloride (102.4 g, 0.4 mol) in toluene is treated with triethylamine (40.5 g, 0.4 mol) over 45 minutes as the temperature rises to 40° C., stirred for 18 hours, and filtered to remove solids. The filtrate is concentrated in vacuo to remove toluene and triethylamine, and the resultant residue is vacuum distilled to give the title product as a colorless liquid (87.0 g, 87% yield, bp 95–98° C./2.6 mmHg)

Using essentially the same procedure, but using the appropriately substituted acetimidoyl chloride, the following compounds are obtained:

| L | M | Q | bp ° C./mmHg | % Yield |
|---|---|---|---|---|
| H | Cl | Cl | 101–104/0.5 | 79 |
| H | CF$_3$ | H | | |
| Cl | H | Cl | 110–112/0.9 | 84 |

EXAMPLE 2

Preparation of 2-(p-Chlorophenyl)-5-(trifluoromethyl)pyrrole-3-carbonitrile

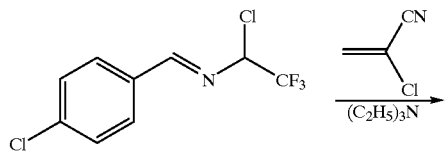

A solution of 1-chloro-N-(p-chloro-benzylidine)-2,2,2-trifluoroethylamine (9.0 g, 0.035 mol) and 2-chloroacrylonitrile (3.7 g, 0.042 mol) in N,N-dimethylformamide is treated dropwise with triethylamine (7.8 g, 0.077 mol) over 45 minutes as the temperature rises to 45° C., stirred at 55–60° C. for 4 hours, stirred overnight at room temperature, and diluted with water and ethyl acetate. The organic layer is separated, washed with water, and concentrated in vacuo to obtain a residue. Flash column chromatography of the residue using silica gel and a 20% ethyl acetate in heptane solution gives the title product as a pale yellow solid (3.9 g, 41.2% yield) which is identified by $^1$H and $^{19}$F NMR.

Following essentially the same procedure, but using the appropriately substituted 1-chloro-2,2,2-trifluoro-N-(substituted benzylidine)ethylamine, the following compounds are obtained:

| L | M | Q | mp° C. |
|---|---|---|---|
| H | CF$_3$ | H | 216–217.5 |
| Cl | H | Cl | |

EXAMPLE 3

Preparation of 2-(3,4-Dichlorophenyl)-5-(trifluoromethyl)pyrrole-3-carbonitrile using 2-chloroacrylonitrile

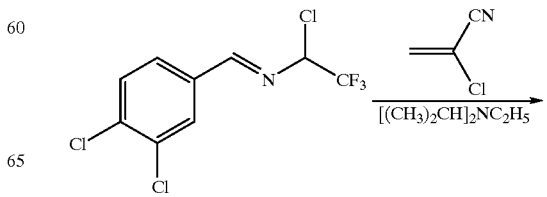

-continued

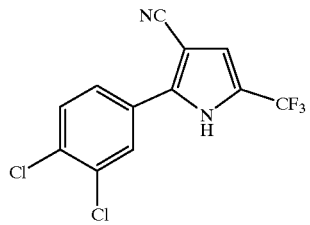

A solution of 1-chloro-N-(3,4-dichlorobenzylidine)-2,2,2-trifluoroethylamine (11.6 g, 0.04 mol) and 2-chloroacrylonitrile (4.2 g, 0.048 mol) in N,N-dimethylformamide is treated dropwise with diisopropylethylamine (12.9 g, 0.1 mol) over 45 minutes as the temperature rises to 40° C., stirred at 55° C. for 4 hours, stirred overnight at room temperature, and diluted with water and ethyl acetate. The organic layer is separated, washed with water, and concentrated in vacuo to obtain a residue. Flash column chromatography of the residue using silica gel and a 20% ethyl acetate in heptane solution gives the title product as a white solid (5.8 g, 47.5% yield) which is identified by $^1$H and $^{19}$F NMR.

EXAMPLE 4

Preparation of 2-(3,4-Dichlorophenyl)-5-(trifluoromethyl)pyrrole-3-carbonitrile using 2,3-dichloropropionitrile

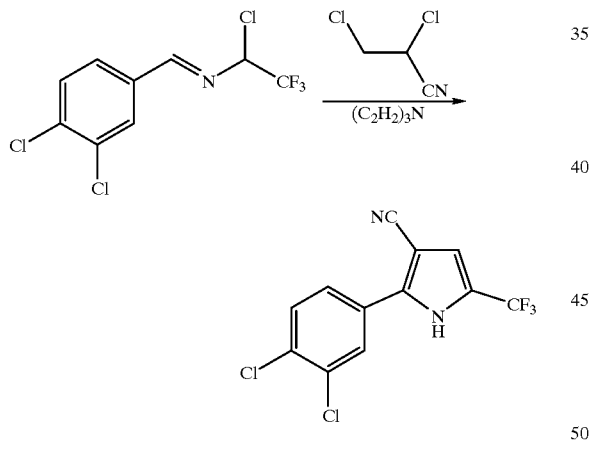

A solution of 1-chloro-N-(3,4-dichlorobenzylidine)-2,2,2-trifluoroethylamine (8.72 g, 0.03 mol) and 2,3-dichloropropionitrile (4.3 g, 0.0345 mol) in N,N-dimethylformamide is treated dropwise with triethylamine (11.1 g, 0.11 mol) over 30 minutes as the temperature rises to 55° C., stirred at 55° C. for 5 hours, cooled to room temperature, and diluted with water and ethyl acetate. The organic layer is separated, washed with water, and concentrated in vacuo to obtain a residue. The residue is dissolved in ethyl acetate and mixed with silica gel. The silica gel mixture is dried in vacuo and washed with a 20% ethyl acetate in heptane solution. The resultant filtrate is concentrated in vacuo and the residue is triturated with heptane and a small amount of ethyl acetate to give the title product as a pale yellow solid (3.2 g, 35% yield).

I claim:
1. A process for the preparation of a 2-aryl-5-(perfluoroalkyl)pyrrole compound having the structural formula I

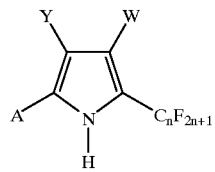

(I)

wherein

W is hydrogen or $C_mF_{2m+1}$;

Y is CN, $NO_2$ or $CO_2R$;

R is $C_1$–$C_4$alkyl;

m and n are each independently an integer of 1, 2, 3, 4, 5, 6, 7 or 8;

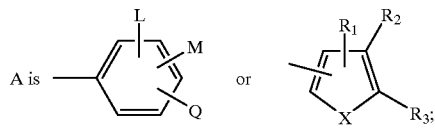

L is hydrogen or halogen;

M and Q are each independently hydrogen, halogen, CN, $NO_2$, $C_1$–$C_4$alkyl, $C_1$–$C_4$haloalkyl, $C_1$–$C_4$alkoxy, $C_1$–$C_4$haloalkoxy, $C_1$–$C_4$alkylthio, $C_1$–$C_4$haloalkylthio, $C_1$–$C_4$alkylsulfinyl, $C_1$–$C_4$haloalkylsulfinyl, $C_1$–$C_4$alkylsulfonyl, $C_1$–$C_4$haloalkylsulfonyl or when M and Q are on adjacent positions they may be taken together with the carbon atoms to which they are attached to form a ring in which MQ represents the structure —$OCH_2O$—, —$OCF_2O$— or —CH=CH—CH=CH—;

$R_1$, $R_2$ and $R_3$ are each independently hydrogen, halogen, $NO_2$, CHO or $R_2$ and $R_3$ may be taken together with the atoms to which they are attached to form a ring in which $R_2R_3$ is represented by the structure

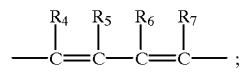

$R_4$, $R_5$, $R_6$ and $R_7$ are each independently hydrogen, halogen, CN or $NO_2$; and X is O or S which process comprises reacting an N-(arylmethylene)-1-chloro-1-(perfluoroalkyl)methylamine compound having the structural formula II (II)

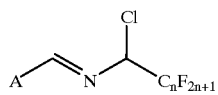

wherein A and n are as described above with a dieneophile compound having the structural formula III or an α,β-dihalo compound having the structural formula IV

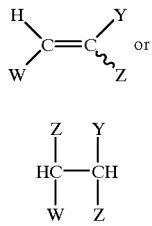

(III)

(IV)

wherein W and Y are as described above and Z is Cl, Br or I, and a base in the presence of a solvent.

2. The process according to claim 1 wherein the base is selected from the group consisting of a tri-($C_1$–$C_6$alkyl) amine, an alkali metal carbonate and a heterocyclic tertiary amine.

3. The process according to claim 2 wherein the base is selected from the group consisting of a tri-($C_1$–$C_6$alkyl) amine, 1,8-diazabicyclo[5.4.0]undec-7-ene, 1,5-diazabicyclo[4.3.0]non-5-ene, 1,4-diazabicyclo-[2.2.2] octane, potassium carbonate and sodium carbonate.

4. The process according to claim 3 wherein the tri-($C_1$–$C_6$alkyl)amine is selected from the group consisting of trimethylamine, triethylamine, tripropylamine, tributylamine and diisopropylethylamine.

5. The process according to claim 1 wherein the solvent is selected from the group consisting of a carboxylic acid amide, a nitrile and a mixture thereof.

6. The process according to claim 5 wherein the solvent is selected from the group consisting of N,N-dimethylformamide and acetonitrile and mixtures thereof dimethylformide, acetonitrile and a mixture thereof.

7. The process according to claim 1 wherein the dieneophile is present in the amount of about one to four molar equivalents and the base is present in the amount of about one to four molar equivalents.

8. The process according to claim 1 wherein the α,β-dihalo compound is present in the amount of about one to four molar equivalents and the base is present in the amount of about two to five molar equivalents.

9. The process according to claim 1 wherein

W is hydrogen;

Y is CN;

n is 1 or 2;

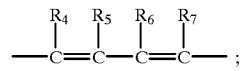

L is hydrogen or halogen; and

M and Q are each independently hydrogen, halogen, $C_1$–$C_4$haloalkyl or $C_1$–$C_4$haloalkoxy.

10. A process for the preparation of an arylpyrrole compound having the structural formula VI

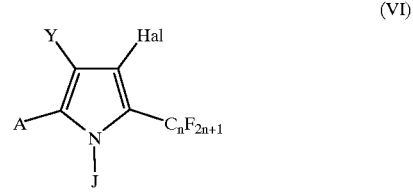

(VI)

wherein

Y is CN, $NO_2$ or $CO_2R$;

R is $C_1$–$C_4$alkyl;

n is an integer of 1, 2, 3, 4, 5, 6, 7 or 8;

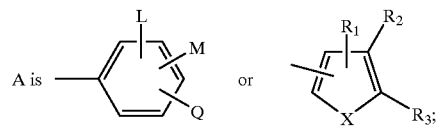

L is hydrogen or halogen;

M and Q are each independently hydrogen, halogen, CN, $NO_2$, $C_1$–$C_4$alkyl, $C_1$–$C_4$haloalkyl, $C_1$–$C_4$alkoxy, $C_1$–$C_4$haloalkoxy, $C_1$–$C_4$alkylthio, $C_1$–$C_4$haloalkylthio, $C_1$–$C_4$alkylsulfinyl, $C_1$–$C_4$haloalkylsulfinyl, $C_1$–$C_4$alkylsulfonyl, $C_1$–$C_4$haloalkylsulfonyl or when M and Q are on adjacent positions they may be taken together with the carbon atoms to which they are attached to form a ring in which MQ represents the structure —$OCH_2O$—, —$OCF_2O$— or —CH=CH—CH=CH—;

$R_1$, $R_2$ and $R_3$ are each independently hydrogen, halogen, $NO_2$, CHO or $R_2$ and $R_3$ may be taken together with the atoms to which they are attached to form a ring in which $R_2R_3$ is represented by the structure

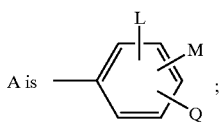

$R_4$, $R_5$, $R_6$ and $R_7$ are each independently hydrogen, halogen, CN or $NO_2$;

X is O or S;

Hal is a halogen atom; and

J is hydrogen or $C_1$–$C_6$alkoxymethyl which process comprises the steps of:

(a) reacting an N-(arylmethylene)-1-chloro-1-(perfluoroalkyl)methylamine compound having the structural formula II

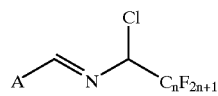

(II)

wherein A and n are as described above with a dieneophile compound having the structural formula VII or an α,β dihalo compound having the structural formula IX

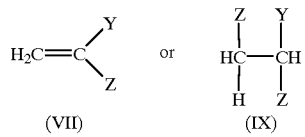

wherein Y is as described above and Z is Cl, Br or I, and a base in the presence of a solvent to form a 2-aryl-5-(perfluoroalkyl)pyrrole compound having the structural formula VIII

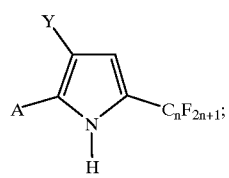

(VIII)

(b) halogenating the formula VIII compound to form the arylpyrrole compound of formula VI wherein J is hydrogen; and (c) optionally alkoxymethylating the formula VI compound wherein J is hydrogen.

11. The process according to claim 10 wherein step (c) comprises reacting the formula VI compound wherein J is hydrogen with a di-($C_1$–$C_6$alkoxy)methane compound, N,N-dimethylformamide and phosphorous oxychloride in the presence of an aprotic solvent to form a reaction mixture and treating the reaction mixture with a tertiary amine.

* * * * *